(12) United States Patent
Rolando et al.

(10) Patent No.: US 11,179,237 B2
(45) Date of Patent: Nov. 23, 2021

(54) VALVULAR SLEEVE FOR VALVULAR PROSTHESES AND CORRESPONDING DEVICE

(71) Applicant: Corcym S.r.l., Milan (IT)

(72) Inventors: Giovanni Rolando, Chivasso (IT); Paolo Gaschino, Castagneto Po (IT)

(73) Assignee: Corcym S.r.l., Milan (IT)

( * ) Notice: Subject to any disclaimer, the term of this patent is extended or adjusted under 35 U.S.C. 154(b) by 0 days.

(21) Appl. No.: 15/746,747

(22) PCT Filed: Jul. 19, 2016

(86) PCT No.: PCT/IB2016/054281
§ 371 (c)(1),
(2) Date: Jan. 22, 2018

(87) PCT Pub. No.: WO2017/013578
PCT Pub. Date: Jan. 26, 2017

(65) Prior Publication Data
US 2018/0214263 A1 Aug. 2, 2018

(30) Foreign Application Priority Data
Jul. 22, 2015 (IT) .................. 102015000037126

(51) Int. Cl.
*A61F 2/24* (2006.01)
(52) U.S. Cl.
CPC .......... *A61F 2/2418* (2013.01); *A61F 2/2412* (2013.01); *A61F 2/2415* (2013.01); *A61F 2/2475* (2013.01); *A61F 2210/0014* (2013.01); *A61F 2210/0076* (2013.01); *A61F 2220/005* (2013.01); *A61F 2220/0033* (2013.01); *A61F 2220/0041* (2013.01); *A61F 2220/0058* (2013.01); *A61F 2220/0075* (2013.01);
(Continued)

(58) Field of Classification Search
None
See application file for complete search history.

(56) References Cited

U.S. PATENT DOCUMENTS

| 3,574,865 A | 4/1971 | Hamaker |
| 3,655,306 A | 4/1972 | Ross et al. |

(Continued)

FOREIGN PATENT DOCUMENTS

| CA | 2664223 C | 6/2008 |
| EP | 1690515 B1 | 7/2008 |

(Continued)

OTHER PUBLICATIONS

Definition of "coextensive" retrieved from https://www.lexico.com/en/definition/coextensive on Aug. 18, 2021 (Year: 2021).*

(Continued)

*Primary Examiner* — Megan Y Wolf
(74) *Attorney, Agent, or Firm* — Eversheds Sutherland (US) LLP; Christopher C. Bolten; Albert K. Heng

(57) ABSTRACT

A valvular sleeve for valvular prostheses including a tubular body extending between an inflow end and an outflow end, the tubular body including a sheet member folded at the outflow end, whereby the tubular body includes an inner tubular portion and an outer tubular portion surrounding the inner tubular portion.

20 Claims, 11 Drawing Sheets

(52) U.S. Cl.
CPC . *A61F 2230/001* (2013.01); *A61F 2230/0067* (2013.01); *A61F 2230/0078* (2013.01); *A61F 2250/0037* (2013.01); *A61F 2250/0039* (2013.01)

(56) References Cited

U.S. PATENT DOCUMENTS

| | | |
|---|---|---|
| 3,739,402 A | 6/1973 | Cooley et al. |
| 4,084,268 A | 4/1978 | Ionescu et al. |
| 4,118,806 A | 10/1978 | Porier et al. |
| 4,265,694 A | 5/1981 | Boretos et al. |
| 4,345,340 A | 8/1982 | Rosen |
| 4,364,126 A | 12/1982 | Rosen et al. |
| 4,364,127 A | 12/1982 | Pierce et al. |
| 4,477,930 A | 10/1984 | Totten et al. |
| 4,501,030 A | 2/1985 | Lane |
| 4,535,483 A | 8/1985 | Klawitter et al. |
| 4,626,255 A | 12/1986 | Reichart et al. |
| 4,680,031 A | 7/1987 | Alonso |
| 4,778,461 A | 10/1988 | Pietsch et al. |
| 4,786,556 A | 11/1988 | Hu et al. |
| 4,816,029 A | 3/1989 | Penny, III et al. |
| 4,888,009 A | 12/1989 | Lederman et al. |
| 4,939,007 A | 7/1990 | Hu et al. |
| 5,032,666 A | 7/1991 | Hu et al. |
| 5,071,431 A | 12/1991 | Sauter et al. |
| 5,084,315 A | 1/1992 | Karimi et al. |
| 5,104,406 A | 4/1992 | Curcio et al. |
| 5,123,919 A | 6/1992 | Sauter et al. |
| 5,139,515 A | 8/1992 | Robicsek |
| 5,147,391 A | 9/1992 | Lane |
| 5,258,023 A | 11/1993 | Reger |
| 5,397,346 A | 3/1995 | Walker et al. |
| 5,397,348 A | 3/1995 | Campbell et al. |
| 5,411,552 A | 5/1995 | Andersen et al. |
| 5,545,215 A | 8/1996 | Duran |
| 5,562,729 A | 10/1996 | Purdy et al. |
| 5,755,782 A | 5/1998 | Love et al. |
| 5,780,807 A | 7/1998 | Saunders |
| 5,876,436 A | 3/1999 | Vanney et al. |
| 5,891,195 A | 4/1999 | Klostermeyer et al. |
| 6,143,025 A | 11/2000 | Stobie et al. |
| 6,171,335 B1 | 1/2001 | Wheatley et al. |
| 6,299,638 B1 | 10/2001 | Sauter |
| 6,352,554 B2 | 3/2002 | De Paulis |
| 6,425,916 B1 | 7/2002 | Garrison et al. |
| 6,709,457 B1 | 3/2004 | Otte et al. |
| 6,716,244 B2 | 4/2004 | Klaco |
| 6,790,229 B1 | 9/2004 | Berreklouw |
| 6,893,459 B1 | 5/2005 | Macoviak |
| 7,186,265 B2 | 3/2007 | Sharkawy et al. |
| 2001/0002445 A1 | 5/2001 | Vesely |
| 2003/0023302 A1 | 1/2003 | Moe et al. |
| 2003/0055496 A1* | 3/2003 | Cai ............... A61F 2/2412 623/2.19 |
| 2003/0114913 A1* | 6/2003 | Spenser .......... A61F 2/2412 623/1.11 |
| 2004/0030381 A1 | 2/2004 | Shu |
| 2004/0186565 A1 | 9/2004 | Schreck |
| 2005/0043790 A1* | 2/2005 | Seguin ............ A61F 2/2403 623/2.18 |
| 2005/0137682 A1 | 6/2005 | Justino |
| 2005/0165479 A1 | 7/2005 | Drews et al. |
| 2005/0240263 A1 | 10/2005 | Fogarty et al. |
| 2006/0271175 A1 | 11/2006 | Woolfson et al. |
| 2007/0255400 A1 | 11/2007 | Parravicini et al. |
| 2008/0091261 A1* | 4/2008 | Long ............... A61F 2/2412 623/1.24 |
| 2013/0197631 A1 | 8/2013 | Bruchman et al. |
| 2014/0249623 A1* | 9/2014 | Matheny .......... A61F 2/2418 623/2.17 |
| 2015/0032205 A1* | 1/2015 | Matheny .......... A61F 2/2415 623/2.15 |

FOREIGN PATENT DOCUMENTS

| | | |
|---|---|---|
| EP | 2399549 A1 | 12/2011 |
| EP | 2572676 A2 | 3/2013 |
| WO | WO9219185 A1 | 11/1992 |
| WO | WO9825549 A1 | 6/1998 |
| WO | 2011109450 A2 | 9/2011 |

OTHER PUBLICATIONS

International Search Report and Written Opinion issued in PCT/IB2016/054281, dated Oct. 14, 2016, 13 pages.
International Preliminary Report on Patentability issued in PCT/IB2016/054281, dated May 2, 2018, 6 pages.
Italian Search Report and Written Opinion issued in IT application No. 102015000037126, completed Apr. 22, 2016, 10 pages, with Translation of Written Opinion.
Akutsu, et al., "Polyurethane Artificial Heart Valves in Animals," Journal of Applied Physiology, Apr. 1959, vol. 14, pp. 1045-1048.
Bernacca, et al., "Hydrodynamic Function of Polyurethane Prosthetic Heart Valves: Influences of Young's Modulus and Leaflet Thickness," Sixth World Biomaterials Congress Transactions, Society for Biomaterials, Minneapolis, Minnesota, 2000, p. 584.
Bernacca, et al., "Polyurethane Heart Valve Durability: Effects of Leaflet Thickness and Material," The International Journal of Artificial Organs, 1997, vol. 20(6), pp. 327-331.
Carbomedics Inc., "Optiform® Mitral Valve Information for Use," Copyright, CarboMedics Incorporated, 2003.
Carbomedics Inc., "Orbis™ Prosthetic Heart Valve Information for Use," Copyright, CarboMedics Incorporated, 2003.
Carbomedics Inc., "Prosthetic Heart Valve Instructions for Use," Copyright, CarboMedics Incorporated, 2003.
Coleman D.L., "Mineralization of Blood Pump Bladders," Transactions of the American Society for Artificial Internal Organs, 1981, vol. 27, pp. 708-713.
Fisher, et al., "A New Design of Polymer Synthetic Leaflet Heart Valve," Sixth World Biomaterials Congress Transactions, Society for Biomaterials, Minneapolis, Minnesota, 2000, 68 pages.
Hanson, et al., "In Vivo Evaluation of Artificial Surfaces with a Nonhuman Primate Model of Arterial Thrombosis," Journal of Laboratory and Clinical Medicine, 1980, vol. 95, pp. 289-304.
Hilbert, et al., "Evaluation of Explanted Polyurethane Trileaflet Cardiac Valve Prostheses," The Journal of Thoracic and Cardiovascular Surgery, Sep. 1987, vol. 94(3), pp. 419-429.
Martin, et al., "Polydimethylsiloxane/Polyether-mixed macrodiol-Based Polyurethane Elastomers: Biostability," Biomaterials, May 2000, vol. 21(10),pp. 1021-1029.
Schoen, et al., "Biomaterial-Associated Calcification: Pathology, Mechanisms, and Strategies for Prevention," Journal of Biomedical Materials Research, Apr. 1988, vol. 22(A1), pp. 11-36.
Thoma, et al., "Ionic Interactions of Polyurethanes," Journal of Biomaterials Applications, Oct. 1988, vol. 3, pp. 180-206.
Ward, et al., "High-Strength, Optically Clear, Silicone-Urethane Thermoplastics for Biomedical Use: Bulk Properties," Sixth World Biomaterials Congress Transactions, Society for Biomaterials, Minneapolis, Minnesota, 2000, p. 431.
Ward R.S., "Thermoplastic Silicone-Urethane Copolymers: A New Class of Biomedical Elastomers," Medical Device & Diagnostic Industry, Apr. 2000.
Ward R.S., "Surface Modification Prior to Surface Formulation: Control of Polymer Surface Properties via Bulk Composition," Medical Plastics and Biomaterials, 1995, vol. 2, pp. 34-41.

* cited by examiner

VALVULAR SLEEVE FOR VALVULAR PROSTHESES AND CORRESPONDING DEVICE

CROSS-REFERENCE TO RELATED APPLICATION

This application is a national stage application of PCT/IB2016/054281, filed Jul. 19, 2016, which claims priority to Italian application 102015000037126, filed Jul. 22, 2015, both of which are herein incorporated by reference in their entirety.

TECHNICAL FIELD

The description relates to valvular prostheses.

One or more embodiments may apply to valvular prostheses, such as valvular heart prostheses.

BACKGROUND

Valvular prostheses are an effective means of treating various pathologies, such as e.g. cardiac valve pathologies, and providing a higher life expectancy and less morbidity in those patients receiving an implanted prosthesis.

An increasing demand thus exists for valvular prostheses which may be produced with a cost-effective manufacturing process.

SUMMARY

An object of one or more embodiments is to meet such a demand.

One or more embodiments may relate to a corresponding prosthetic valvular device, including e.g. a valvular sleeve coupled with a stent.

The claims are an integral part of the disclosure of embodiments as provided herein.

BRIEF DESCRIPTION OF THE DRAWINGS

One or more embodiments will now be described, by way of example only, with reference to the annexed figures, in which.

Figure 1:
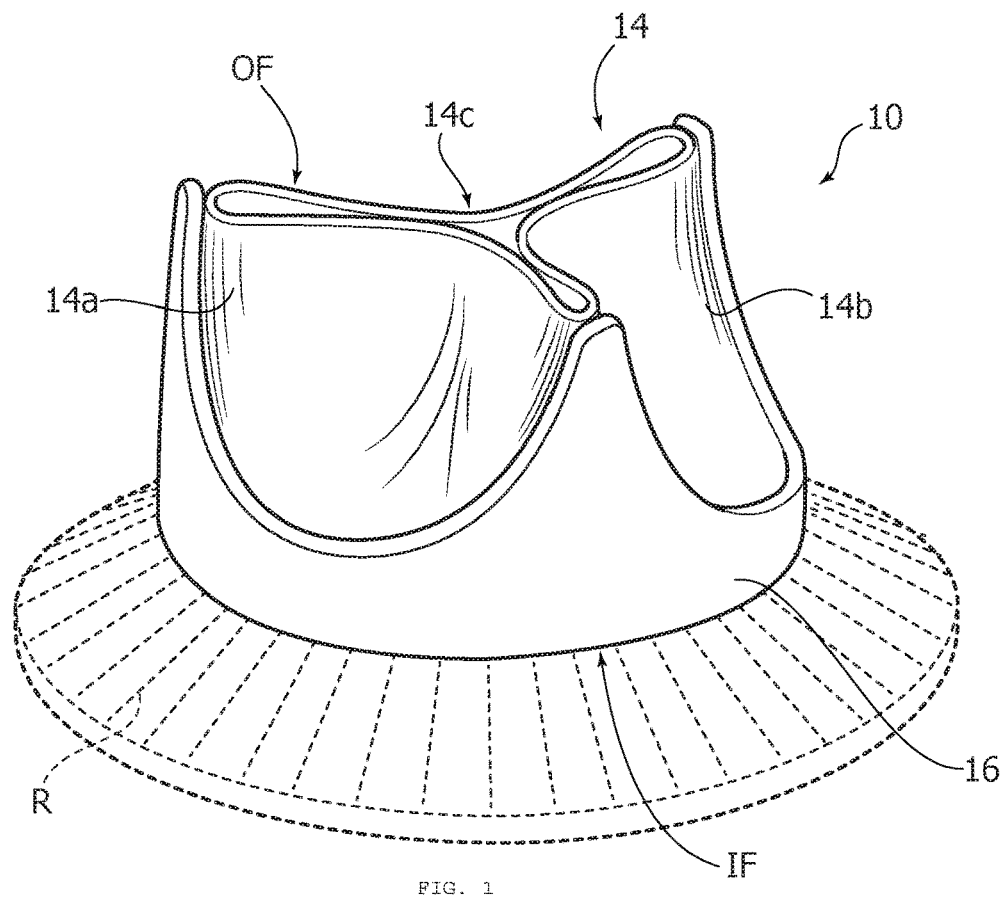
FIGS. 1 and 2 are exemplary representations of prosthetic valvular devices.

It will be appreciated that, for the sake of clarity, one or more of the figures may not be drawn to a same scale.

DETAILED DESCRIPTION

In the ensuing description, one or more specific details are illustrated, aimed at providing an in-depth understanding of examples of embodiments. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the scope of protection or the scope of the embodiments.

In the figures, reference numeral 10 indicates a valvular prosthesis.

In one or more embodiments, the prosthesis may be adapted for implantation at a valvular site of a patient. A heart annulus, such as e.g. an aortic annulus, may be exemplary of such an implantation site. A pulmonary valvular annulus may be exemplary of another site for implantation of a valvular heart prosthesis. A mitral valvular annulus may be exemplary of a further site for implantation of such an implantation site.

The embodiments are not limited to possible use as a heart valvular prosthesis. Other exemplary implantation sites may include, e.g. various sites in the blood circulatory system, both arterial and venous.

In one or more embodiments, the prosthesis 10 may include a valvular sleeve 14.

In one or more embodiments, the valvular sleeve 14 may include a tubular body intended to define a flow conduit (e.g. a conduit for the flow of blood) between an inflow end IF and an outflow end OF.

In one or more embodiments, the valvular sleeve 14 may include one or more (e.g., a plurality) a plurality of valve leaflets. For example, an embodiment having three leaflets, indicated as 14a, 14b and 14c, are shown by way of example in the drawings. The one or more valve leaflets 14a, 14b, 14c may extend from the inflow end IF towards the outflow end OF (that is distally of the inflow end IF) and is displaceable under fluid pressure, e.g. blood pressure:

radially outwardly to permit fluid flow from the inflow end IF to the outflow end OF of the valvular sleeve 14 (upward direction, in the figures), and radially inwardly to impede or obstruct fluid flow in the opposite direction, namely from the outflow end OF to the inflow end IF of the valvular sleeve 14 (downward direction, in the figures).

In one or more embodiments, the valvular sleeve 14 may reproduce operation of a natural valve, e.g. with the leaflets 14a, 14b, 14c adapted to deform:

to an inward coapting condition to impede fluid (e.g. blood) flow from the outflow end OF to the inflow end IF, and to an outward expanded condition to permit fluid (e.g. blood) flow from the inflow end IF towards the outflow end OF.

It will be appreciated that the designations "inflow end" and "outflow end" refer to the direction of unimpeded fluid flow through the valve prosthesis 10.

In one or more embodiments, the valvular sleeve 14 may be coupled with a supporting armature 16, currently referred to as "stent", which is intended to support the (generally flexible) valvular sleeve 14.

Figure 3:
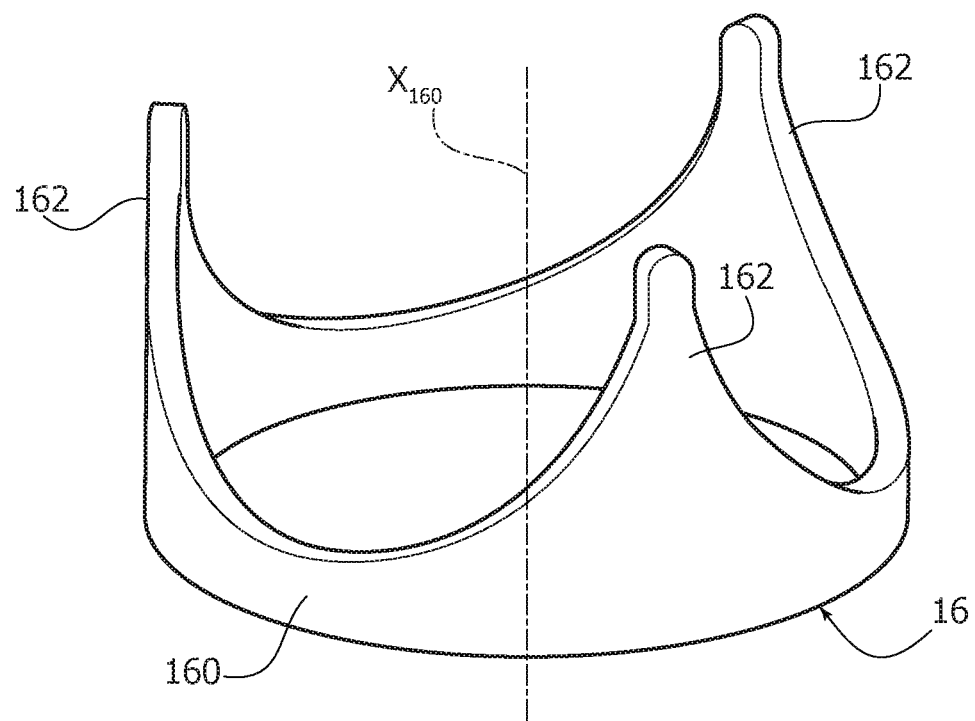
FIGS. 3 and 4 are exemplary representations of stents for prosthetic valvular devices.
Figure 4:
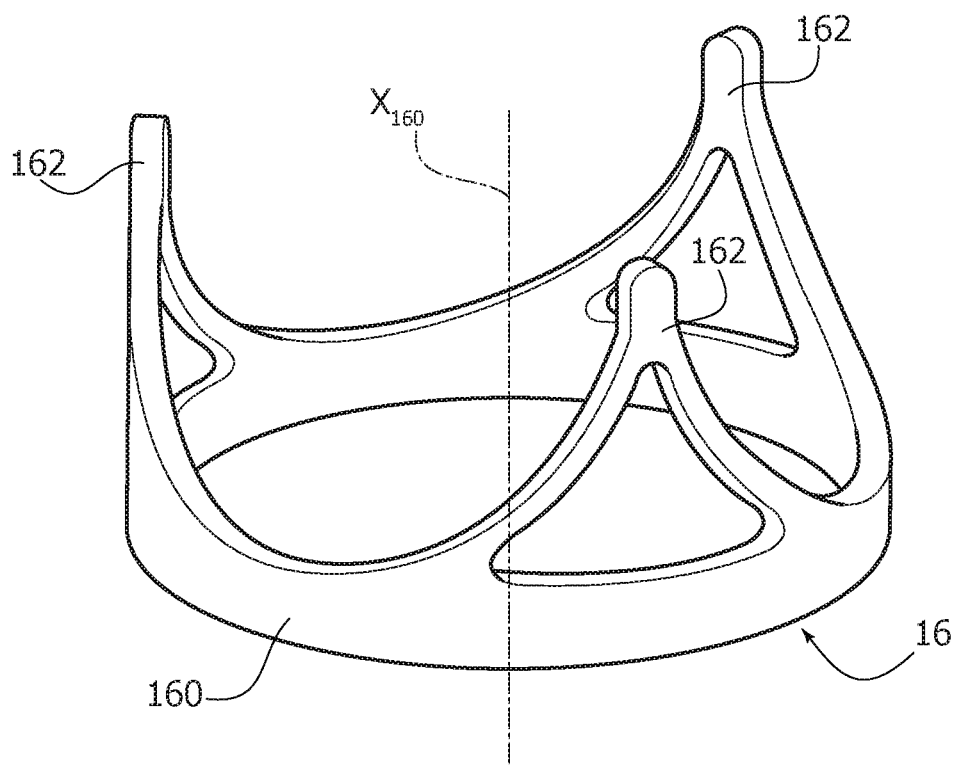

FIGS. 3 and 4 are exemplary of stents 16 adapted for use with valvular sleeves 14 including three leaflets 14a, 14b, 14c.

Stents 16 as exemplified in FIGS. 3 and 4 may be (substantially) rigid or flexible. Stent materials may include metals (e.g. titanium, cobalt-chrome alloys, Nitinol) or polymers (e.g. Polyoxymethylene (POM) such as Delrin® or polycarbonate).

Stent configurations may vary depending on the material of the stent. It will be appreciated that a wide variety of biocompatible materials may be incorporated into stents 16.

For instance, FIG. 3 is exemplary of a solid (e.g. non-apertured) structure which may be adapted for use for e.g. a polymer stent.

The open (e.g. apertured) configuration of FIG. 4 may be adapted for use e.g. for a metal stent 16.

One or more embodiments may include network-like stent structures, e.g. for valvular prostheses intended to be (e.g. radially) collapsed in view of implantation: EP-A-1 690 515 A1 is exemplary of a valvular prosthesis including such a collapsible stent.

Figure 2:
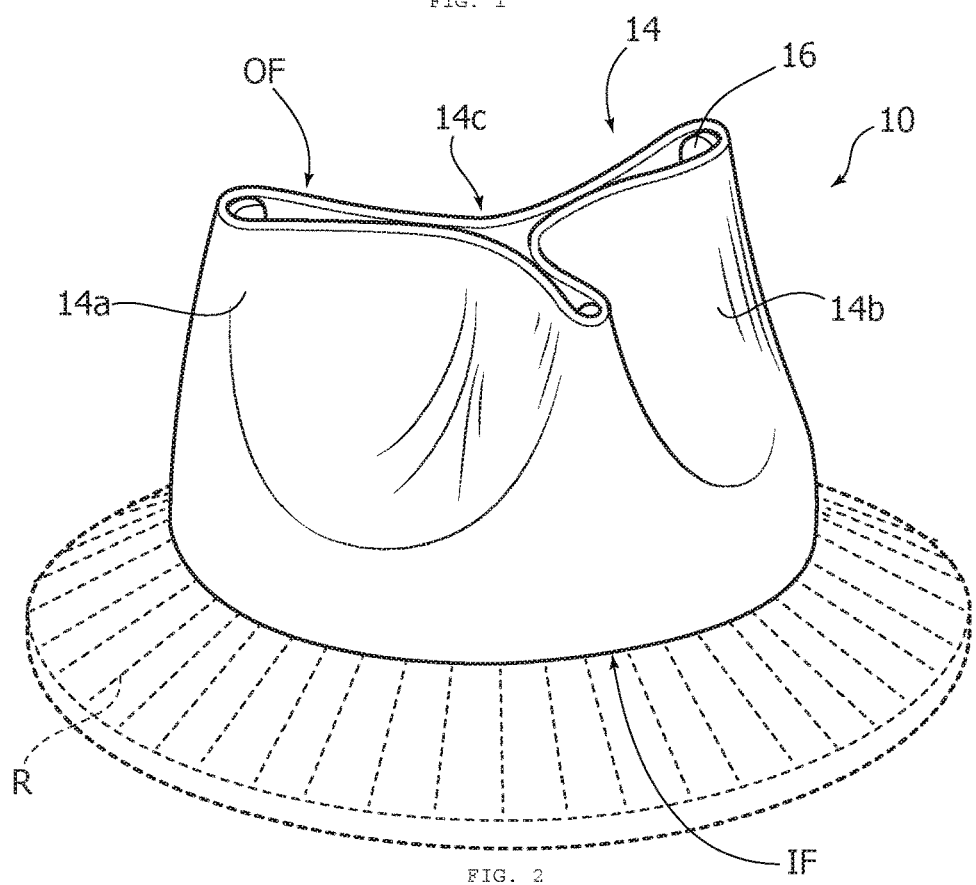

In one or more embodiments, coupling a valvular sleeve 14 with a stent 16 may be either with the stent 16 surrounding (e.g., radially outside of) the valvular sleeve 14 as schematically represented in FIG. 1 (and FIGS. 26 to 28) or with the valvular sleeve 14 surrounding the stent 16 as schematically represented in FIG. 2. In one or more embodiments, the stent 16 may be at least partly "sandwiched" between two portions of the valvular sleeve 14, e.g. as better detailed in the following. In a further embodiment, the valvular sleeve 14 may be "sandwiched" between two portions of the stent 16.

In one or more embodiments, the stent 16 may include a ring-like body 160 intended to be located at the inflow end IF of the valvular sleeve 14 and a plurality of posts or prongs 162 extending from the base body 160 in a distal direction from the inflow end IF towards the outflow end OF of the valvular sleeve 14.

In the exemplary configurations of FIGS. 1 to 4, the stent 16 may include three posts or prongs 162 equally spaced 120° around the circumferential extension of the base body 160, that is equally angularly spaced around the main axis $X_{160}$ of the annular body 160 (and the stent 16 as a whole).

FIGS. 3 and 4 are exemplary of embodiments wherein the stent 16 includes a proximal (e.g. inflow) edge or rim extending along a circular line centered around a main axis $X_{160}$ and a distal (e.g. outflow) edge or rim extending along a scalloped line, that is an arched line connecting the distal ends of the prongs 162.

In one or more embodiments, the leaflets 14a, 14b, 14c of the valvular sleeve 14 may have a semi-lunar (half-moon), scoop-like shape so that each leaflet 14a, 14b, 14c in turn includes a proximal, crescent-shaped margin essentially co-extensive with one of the scallops of the stent 16 as well as a distal margin adapted to coapt with the distal margins of the other leaflets when the valvular sleeve is in the "closed" condition, which impedes fluid flow from the outflow end OF towards the inflow end IF.

In one or more embodiments (e.g. in so-called "stentless" valvular prostheses) a stent 16 may not be present, thus providing a valvular prosthesis of high flexibility.

In one or more embodiments, a valvular prosthesis may include various other elements in addition to the valvular sleeve 14 or the prosthetic valvular device (valvular sleeve 14 plus stent 16) as considered herein.

These other elements may include e.g. a sewing ring R (as exemplified in phantom lines in FIGS. 1 and 2), one or more sealing skirts, and other structures intended to facilitate delivery and/or implantation of the prosthesis at the implantation site.

The concepts and principles outlined in the foregoing are generally known in the art, thus making it unnecessary to provide a more detailed description herein.

One or more embodiments may take advantage of the possibility of producing the valvular sleeve 14 of a flexible material which may be in the form of e.g. a planar sheet member or a tubular member as better detailed in the following.

Materials adapted to provide a desired degree of flexibility of the valvular sleeve 14 may include e.g.

fabrics produced e.g. by knitting, weaving or felting fibers, including "non-woven" materials, sheet or laminar materials produced e.g. by lamination, molding or dipping.

One or more embodiments may employ sheet or laminar material reinforced by fibers, such as e.g. carbon fibers or Kevlar® fibers.

Materials adapted for use in one or more embodiments may include e.g.:

biocompatible polymers, such e.g. as silicone, polyethylene, polypropylene, polytetrafluoroethylene (PTFE), polyethylene terephthalate (PET) such as Dacron®;

biological materials such as e.g. bovine, porcine or equine pericardium.

Materials produced by "tissue-engineering" technologies may represent an option for one or more embodiments.

In one or more embodiments, the valvular sleeve 14 may be coated with a biocompatible coating e.g. a carbonaceous biocompatible coating. Such a coating may extend over the whole sleeve or only over part of it e.g. the part exposed to blood flow.

In one or more embodiments, as exemplified in FIGS. 5A, 5B, 6 and 7, such flexible material (e.g. a fabric material) may be formed to a tubular sheet member T.

Figure 5A:
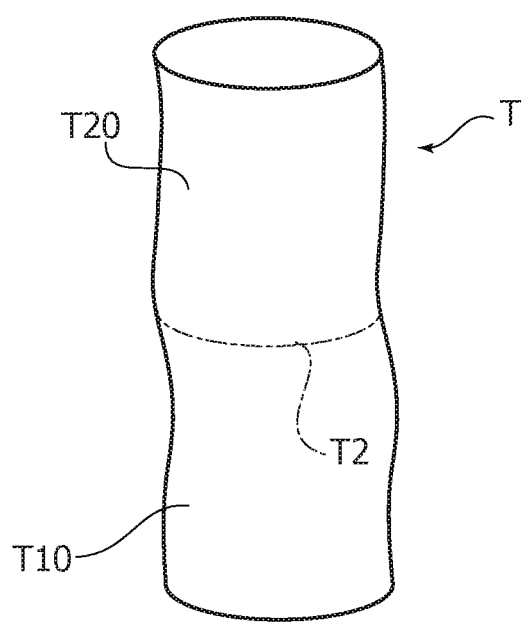
FIGS. 5A, 5B, 6 and 7 are exemplary of the production of valvular sleeves for valvular prostheses according to one or more embodiments.
Figure 5B:
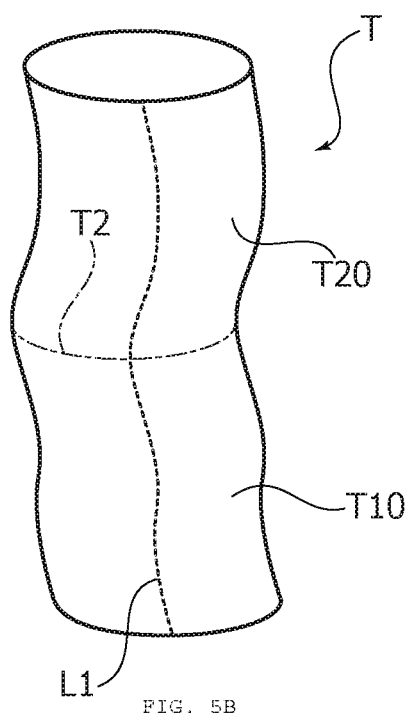

FIGS. 5A and 5B are schematically representative of such a tubular sheet member T which may be either produced as such (e.g. as a knitted fabric) as schematically shown in FIG. 5A or produced by folding into a tube a sheet member which is then closed along a longitudinal joining line L1 (e.g. by stitching or welding) as schematically shown in FIG. 5B Tubular sheet members T as schematically represented in FIGS. 5A and 5B may be similar to vascular grafts as currently used e.g. in replacing portions of blood vessels or other types of body lumen.

Figure 6:
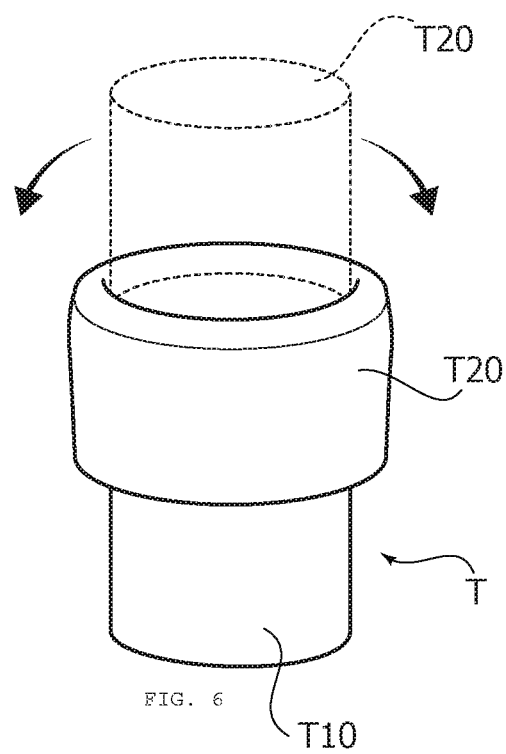

FIG. 6 is schematically representative of the possibility of "overturning" or everting such a tubular sheet element to obtain a double-walled annular (tubular) member adapted to produce a valvular sleeve 14.

Figure 7:
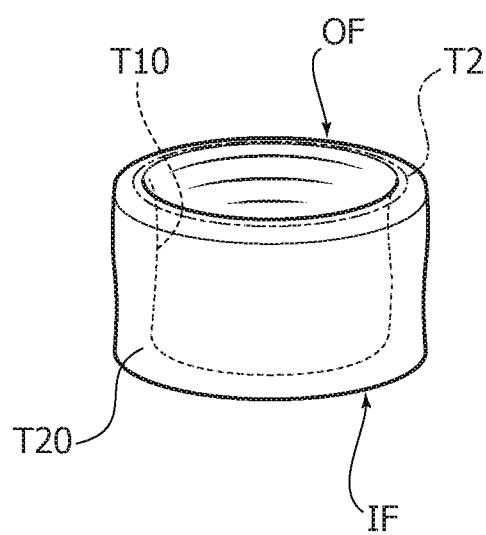

As exemplified in FIGS. 5A and 5B, a tubular sheet member T may be regarded as including two longitudinally adjacent (subsequent) sections T10, T20 with e.g. the second section T20 adapted to be overturned outwardly with respect to the first section T10 as schematically represented in FIG. 6 to produce the tubular body of FIG. 7. There, the section T20 surrounds the section T10, so that the portions T10, T20 form the inner portion and the outer portion, respectively, of a double-walled tubular body as shown in FIG. 7.

An essentially identical result may be obtained with the second section T20 overturned inwardly of the first section T10, so that the section T10 will surround the section T20, with the portions T10, T20 forming then the outer portion and the inner portion, respectively, of the double-walled tubular body of FIG. 7.

In one or more embodiments, the overturning process of FIG. 6 (however performed, inwardly or outwardly) may lead to the two sections T10, T20 lying one inside the other with the line T2 at which overturning has taken place located at one of the ends of the tubular body shown in FIG. 7.

In one or more embodiments, the two sections T10, T20, i.e. the inner and outer portions of the tubular body of FIG. 7, may be of a same length or different lengths. In one or more embodiments these inner and outer sheets may be trimmed to a same length (height) by cutting the portion of the longer sheet protruding with respect to the shorter sheet.

FIGS. 8 to 11 are exemplary of another approach for producing a tubular body essentially as depicted in FIG. 7.

Figure 8:
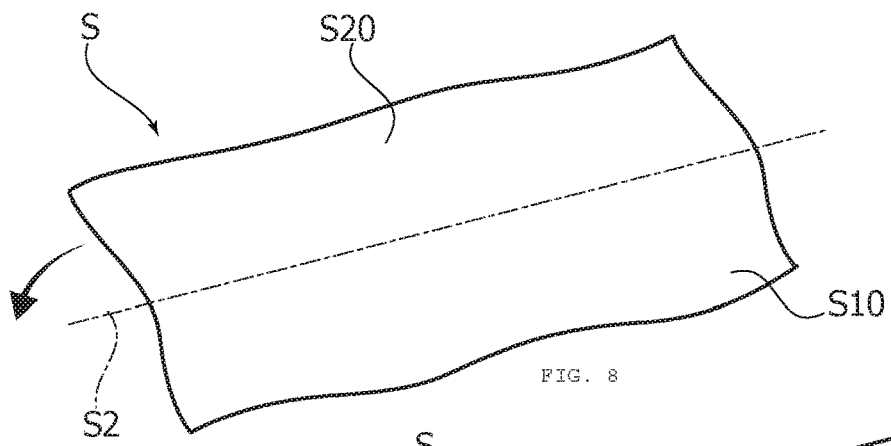
FIGS. 8 to 11 are exemplary of the production of valvular sleeves for valvular prostheses according to one or more embodiments.
Figure 9:
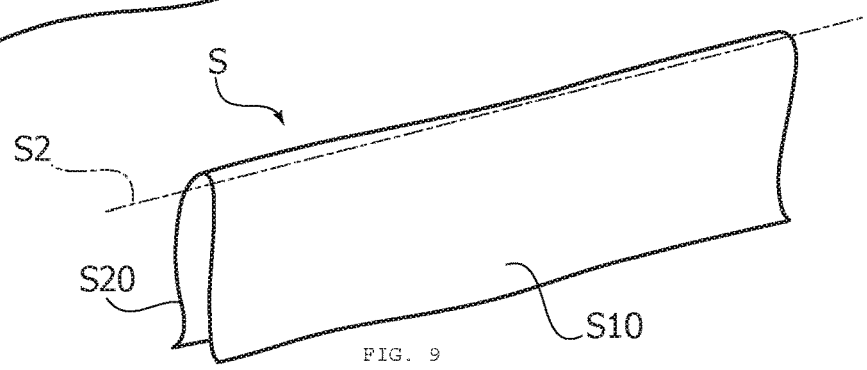

In one or more embodiments as exemplified in FIGS. 8 to 11 such a tubular body may be produced by using (instead of a tubular sheet member T as shown in FIGS. 5A and 5B) a planar sheet member S (e.g. of a rectangular or square shape) which may be U-folded at a folding line S2 as schematically shown in FIG. 9 to produce a U-folded sheet member including two sections S10, S20 facing each other in the U-shape.

Figure 10:
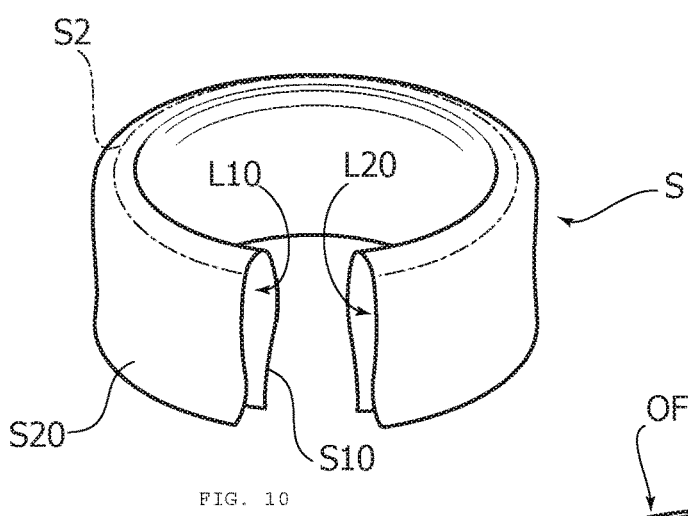

Such a U-shaped sheet member as shown in FIG. 9 may then be handled as a sort of band or ribbon and brought to a ring or collar shape as schematically shown in FIG. 10. This shaping into a ring or collar will result in the opposed end edges L10, L20 of the U-shaped sheet member of FIG. 9 being arranged facing each other.

Figure 11:
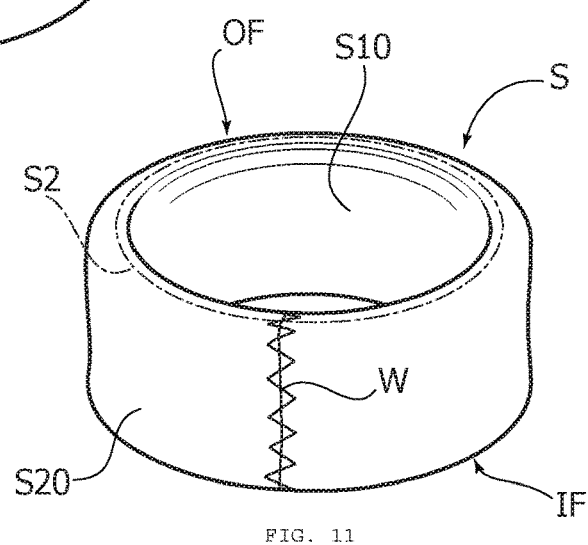

The end edges L10, L20 may then be joined to each other (e.g. via stitching, adhesive, welding, including ultrasound welding) along a joining line W to again produce a double-walled tubular body as shown in FIG. 11 including an outer portion and an inner portion corresponding to the portions S10, S20 originally arranged side-to-side of the sheet member S of FIG. 8.

Whether the portion S10 or the portion S20 will constitute the inner or the outer portion of the tubular body of FIG. 11 will depend, e.g. on the direction of shaping into a ring or collar the U-shaped sheet member of FIG. 9 as schematically shown in FIG. 10.

In one or more embodiments, joining the opposed end edges L10, L20 of the U-folded sheet member of FIG. 9 shaped into a ring or collar as shown in FIG. 10 may involve both the inner and outer portions S10, S20. In one or more embodiments such joining may involve only one of these portions (e.g. S10 or S20).

In one or more embodiments, the process as described (however performed, i.e. irrespective of the direction of shaping into a ring or collar of FIG. 10) may lead to the two portions S10, S20 lying one inside the other with the line S2 at which the sheet member of FIG. 8 has been folded located at one of the ends of the tubular body shown in FIG. 11.

Again, in one or more embodiments the two portions S10, S20, i.e. the inner and outer portions of the tubular body of FIG. 11 may be of equal or different widths (orthogonal to the folding line S2). In one or more embodiments, these inner and outer portions may again be trimmed to a same length (height) by cutting the portion of the longer sheet protruding with respect to the shorter sheet.

Figure 12:
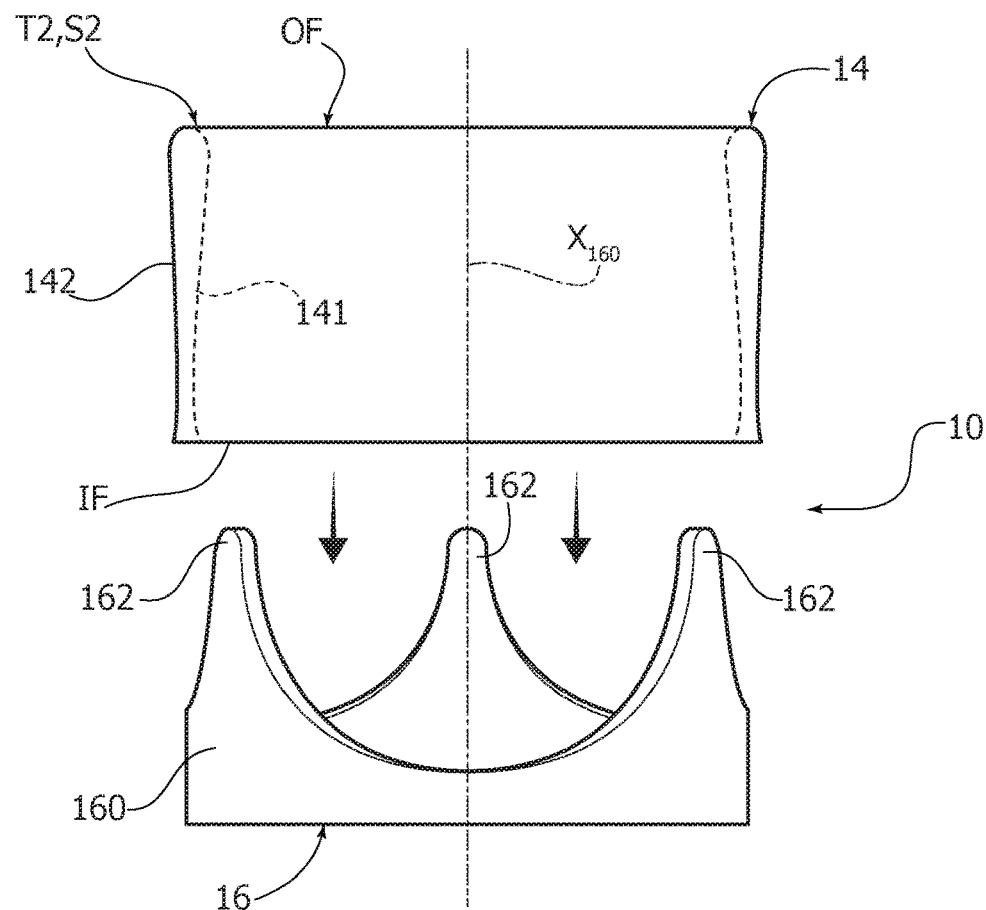
FIGS. 12 and 13 are exemplary of coupling a valvular sleeve of one or more embodiments with a stent.

FIG. 12 is schematically exemplary of fitting a tubular body as exemplified in FIG. 7 or FIG. 11 onto a stent 16 (e.g. a stent as exemplified in FIG. 3) so that the tubular body of FIG. 7 or FIG. 11 may be included as a valvular sleeve 14 in a prosthetic valvular device 10.

In one or more embodiments, such a valvular sleeve 14 for valvular prostheses may include a tubular body (e.g. as shown in FIGS. 7 and 11) extending between an inflow end IF and an outflow end OF of the valvular sleeve 14, with such a tubular body including an inner portion 141 and an outer portion 142. As used herein, "inner" and "outer" refer to the radial direction of the sleeve 14, e.g. with the outer portion 142 surrounding (e.g. radially outside of) the inner portion 141.

In one or more embodiments:
the inner portion 141 may include e.g. the first section T10 (resp. the second section T20) of the tubular sheet member T or the first portion S10 (resp. the second portion S20) of the sheet member S,
the outer portion 142 may include e.g. the second section T20 (resp. the first section T10) of the tubular sheet member T or the second portion S20 (resp. the first portion S10) of the sheet member S.

Whatever the specific arrangement, a tubular body as per FIG. 7 or FIG. 11 may be fitted onto a stent 16 in such a way that the overturning line T2 or the folding line S2 may be located at the outflow end OF of the valvular sleeve 14.

In that way (see e.g. FIGS. 12 and 13) the overturning line T2 or the folding line S2 may be located at the distal margins of the leaflets 14a, 14b, 14c, that is—as indicated previously—at the margins adapted to coapt when the valvular sleeve is in the closed position which impedes fluid flow from the outflow end OF towards the inflow end IF.

Due to the inner and outer portions 141, 142 being formed by overturning/folding a sheet-like member (possibly formed into a tube) the inner portion 141 and outer portion 142 will be formed out of a single sheet member having a loop or fold extending around the outflow end OF between the inner and outer portions 141, 142. The inner and outer portions 141, 142 are parts of a same laminar (sheet-like) body e.g. of a fabric material or the like, with a loop or fold at the overturning line T2/folding line S2 located at (e.g. extending around) the outflow end OF of the sleeve 14.

In one or more embodiments, by using a single sheet of material overturned or folded upon itself, the inner and outer portions 141, 142 will not require to be joined at the outflow end OF of the sleeve 14 by resorting to e.g. stitching, gluing, welding and so on, as required if two separate sheets were joined at the outflow end OF of the sleeve 14.

In one or more embodiments, the two portions 141, 142 being already connected at the overturning line T1 or the folding line S2 "originally", e.g. due to being formed as one piece of fabric or other laminar material, will avoid any sort of cutting (followed by stitching, gluing, welding and so on) as possibly needed to connect two separate portions 141 and 142. In one or more embodiments, the drawbacks possibly related e.g. to fibres of a fabric cut becoming loose, sharp edges or protrusions formed by cutting, stitching, gluing, welding may thus be avoided.

FIG. 12 is exemplary of a way of coupling the valvular sleeve 14 to a stent 16 by taking advantage of the valvular sleeve 14 being a double-walled structure including an inner portion 141 and an outer portion 142 with a loop or fold therebetween.

Figure 13:
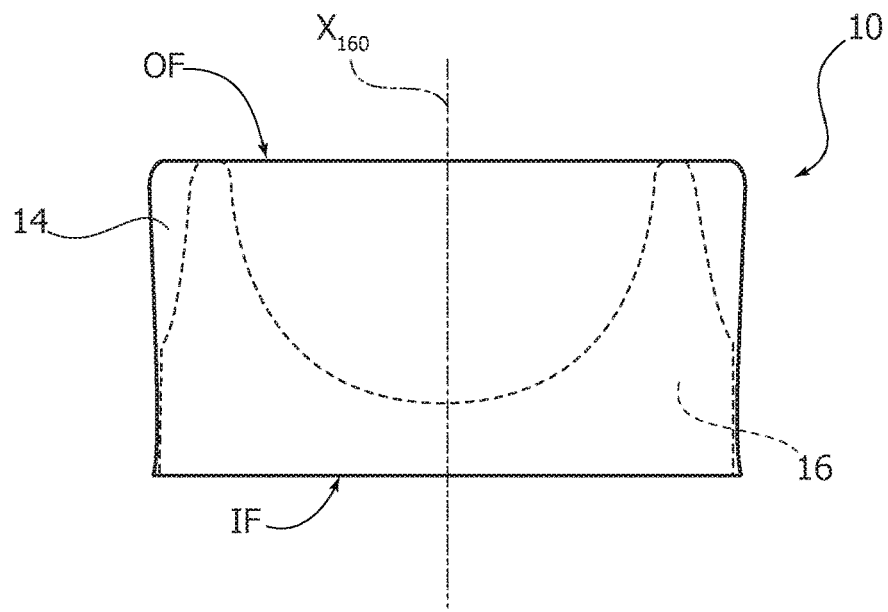

In one or more embodiments the valvular sleeve 14 may be vested onto the stent 16 as schematically shown in FIG. 13, e.g. by simply letting the stent 16 extend in the (inverted) U-shape or channel shape of the structure of the valvular sleeve 14.

In that way, the valvular sleeve 14 may be retained onto the stent 16 against any force urging the valvular sleeve 14 in the proximal direction (outflow to inflow, e.g. downward in FIG. 13) without any other form of coupling (e.g. stitching, and so on) being required for that purpose. Such a sort of a form coupling may facilitate the action of the prosthetic valvular device 10 in impeding undesired proximal flow (e.g. of blood) from the outflow end OF towards the inflow end IF.

As noted previously e.g. in connection with FIGS. 12 and 13, in one or more embodiments the overturning line T2 or the folding line S2 may be located at the distal margins of the (double-walled) leaflets 14a, 14b, 14c.

Various types of coupling of the valvular sleeve 14 to the stent 16 may be otherwise envisaged e.g. as exemplified in the following.

Also, while possible coupling of the valvular sleeve 14 to a stent 16 to form a prosthetic valvular device has been exemplified here, the valvular sleeve 14 may be included in a "stentless" valvular prosthesis without being coupled to a stent.

Also, coupling with a stent 16 has been exemplified in FIGS. 12 and 13 with the stent 16 extending between the inner sheet 141 and the outer sheet 142 of the valvular sleeve 14. Other embodiments as exemplified in FIGS. 1 and 2 may provide for a stent 16 being configured either for surrounding the valvular sleeve 14 (e.g. as better detailed in the following) or for being surrounded by the valvular sleeve 14.

Whatever the embodiments (e.g. a "stentless" arrangement or a "stented" arrangement involving coupling with a stent 16, with the stent 16 arranged inside, outside or inserted between the inner and outer portions 141, 142 of the valvular sleeve 14), the (double-walled) leaflet portions 14a, 14b, 14c may be shaped to a desired semi-lunar (e.g. eyelid-shaped) scoop-like form as exemplified e.g. in FIGS. 1 and 2 with such shape retained in the absence of any fluid force applied thereto. This may be the condition in which the valvular sleeve 14 may be stored e.g. mounted in a holder in a container or in an implantation kit to be made available at the implantation theatre.

Such shaping of the leaflets may be by known means including e.g. mechanical shaping, liquid pressure, application of heat or combinations of these. The nature of the sheet material (e.g. fabric or tissue) of the valvular sleeve 14 may dictate or limit available options for the technique(s) adopted for shaping the leaflets.

Figure 14:
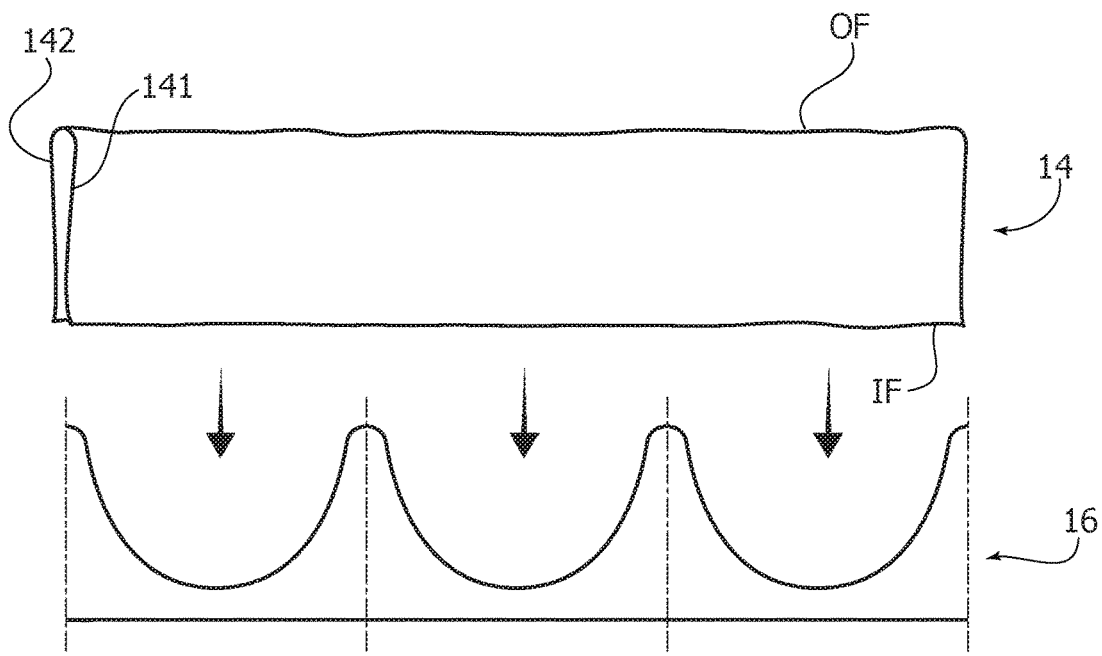
FIGS. 14 to 18 are further exemplary of coupling a valvular sleeve of one or more embodiments with a stent.

FIG. 14 reproduces for the sake of simplicity the same situation as depicted in FIG. 12 (namely the possible coupling of the valvular sleeve 14 with a stent 16). In FIG. 14 the valvular sleeve 14 and the stent 16 are shown in a notional expanded circumferential view, that is in a notional deployed plane view, as would result by cutting the substantially cylindrical shape of the prosthetic device 10 along one of its generating lines and letting the device 10 lie flat on a plane.

FIGS. 15 to 18 are exemplary of various embodiments where the inner and outer portions 141, 142 of the valvular sleeve 10 may be joined at various points, e.g. via stitching, adhesive, welding, including ultrasound welding. While most of the examples illustrated in FIGS. 15 to 18 (and FIGS. 20 to 28) refer to a prosthetic valvular device including a valvular sleeve 14 coupled with a stent 16, the relative disclosure will identically apply to a "stentless" valvular sleeve 14, that is a valvular sleeve 14 intended to be used in a valvular prosthesis without coupling with a stent 16.

Figure 15:
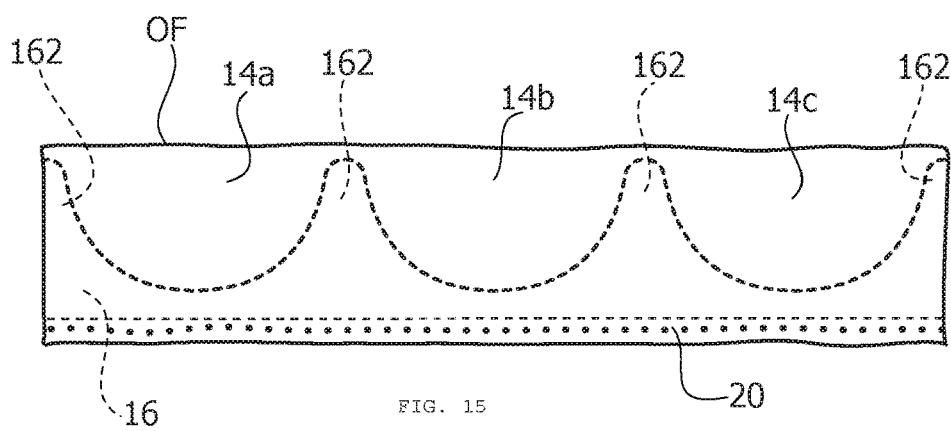

FIG. 15 exemplifies the possibility of joining (e.g. by stitching, adhesive, welding including ultrasound welding: hereinafter all these exemplary possibilities will be referred simply as "joining") the inner and outer portions 141, 142 with a continuous or discontinuous, e.g. point-wise, joining line 20 extending along the inflow end IF of the valvular sleeve 14.

In that way, the inner and outer portions 141, 142 formed of a single piece of sheet material with a loop therebetween at the outflow end OF (that is, at the distal margins of the leaflets 14a, 14b, 14c) will also be joined—by a positive seam as represented the joining line 20—at the inflow end IF so that the double-walled structure of the valvular sleeve 14 may be closed (also) at the inflow end IF.

A joining line 20 as exemplified in FIG. 15 may join the inner portion 141 and the outer portion 142 by extending longitudinally or axially outwardly of the stent 16 (if present), such that the stent is not located between the inner portion 141 and outer portion 142 of the sleeve 14. Alternatively, the joining line 20 may extend to the stent 16, e.g. in the form of stitches extending through apertures (e.g. holes) in the stent 16. In this embodiment, all or portions of the stent may be located or "sandwiched" between the inner and outer portions 141, 142.

Figure 16:
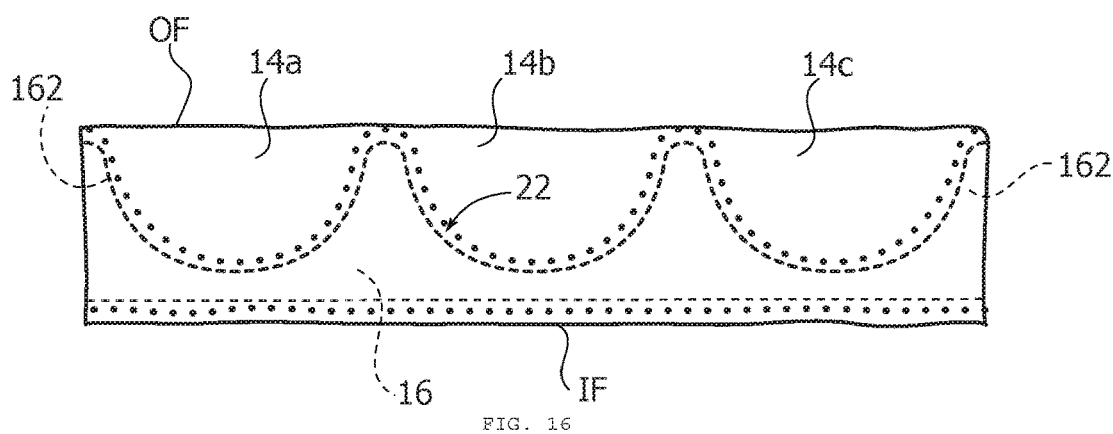

FIG. 16 is exemplary of the possibility of providing a joining line 22 (again adapted to be produced with any of the exemplary joining techniques considered in the foregoing) extending along a scalloped trajectory more or less closely following the crescent-shaped proximal margins of the leaflet portions of the inner and outer sheets 141, 142: these leaflet portions of the portions 141 and 142 of the tubular body of the sleeve are indicated with the same references 14a, 14b, 14c used for the valve leaflets as shown e.g. in FIGS. 1 and 2.

FIG. 16 shows that the joining line 22 may extend arcuately between the prongs 162 of the stent thus forming the so-called "commissures" of the valvular sleeve 14. In some embodiments, both joining line 20 (FIG. 15) and joining line 22 (FIG. 160) are used to capture the stent 16 between a portion of the inner and outer portions 141, 142 of valvular sleeve 14.

Figure 17:
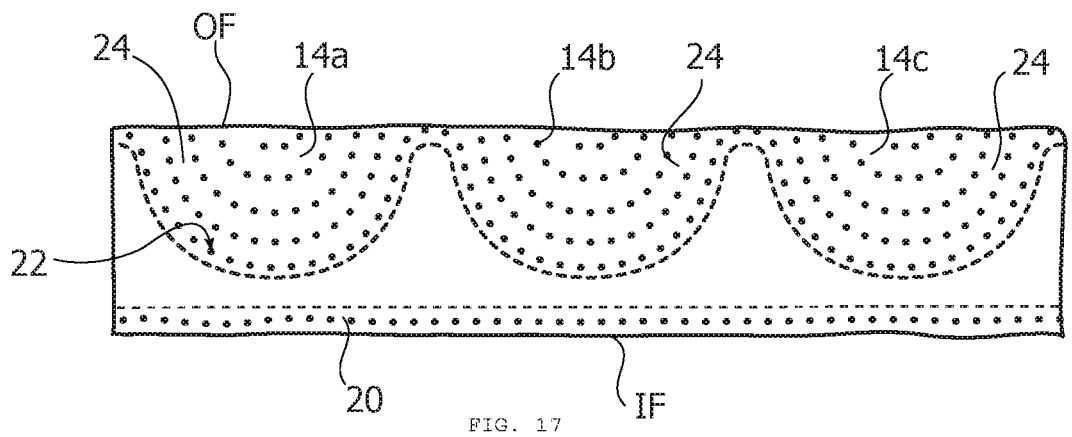
Figure 18:
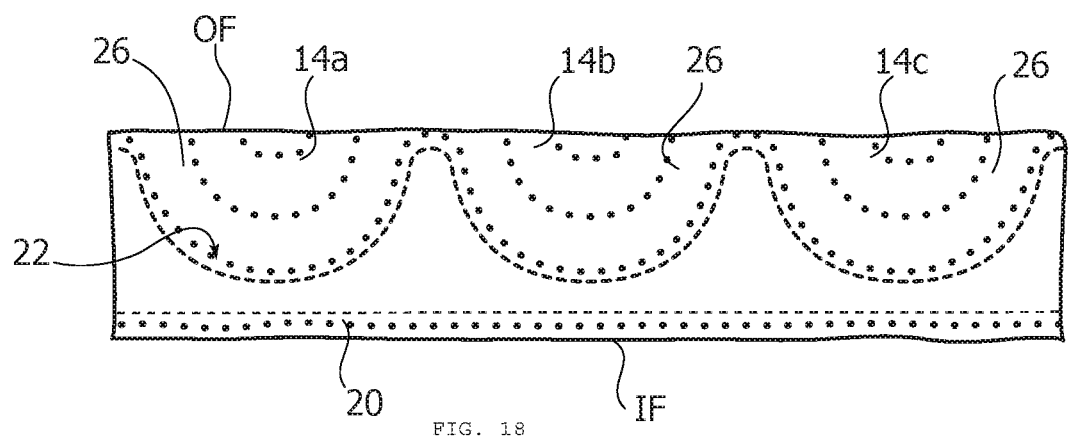

FIGS. 17 and 18 are exemplary of the possibility of forming joining lines 24 and 26 to join the inner and outer portions 141, 142 within their leaflet portions 14a, 14b, 14c. In each Figure, a series of concentric arcuate joining lines, comprising progressively smaller arcuate lengths, is provided from the proximal leaflet margins adjacent to the stent 16 to an outermost arcuate length near distal leaflet margins (i.e., the margins that coapt to impede fluid flow from the outflow end OF to the inflow end IF). It will be appreciated that other joining lines (e.g., parallel, perpendicular, or otherwise angled with respect to the axis $X_{160}$ of the valve, may be used in alternative embodiments.

By resorting to such an arrangement, the leaflets (which are double-walled due to the presence of the inner portion 141 and the outer portion 142) will behave in fact as a single (layered) laminar body e.g. avoiding the formation of pockets between the inner and outer portions 141, 142.

Also, the joining lines 24, 26 may be beneficial in facilitating bestowing onto the leaflet portions 14a, 14b, 14c their concave scoop-like configuration as exemplified in FIGS. 1 and 2 and/or in facilitating retention of such a configuration as possibly imparted with other means as discussed previously.

The pattern of the joining lines 24, 26 (which may be either continuous or discontinuous, e.g. point-wise as exemplified in FIGS. 17 and 18) may facilitate achieving/retaining a certain shape and may include e.g. radial lines with respect to the half-moon shape of the leaflets 14a, 14b, 14c as shown in FIG. 17 or extend along scalloped trajectories somewhat reproducing the scalloped trajectory of the joining line 22 at the proximal margins of the leaflets 14a, 14b, 14c.

Figure 19:
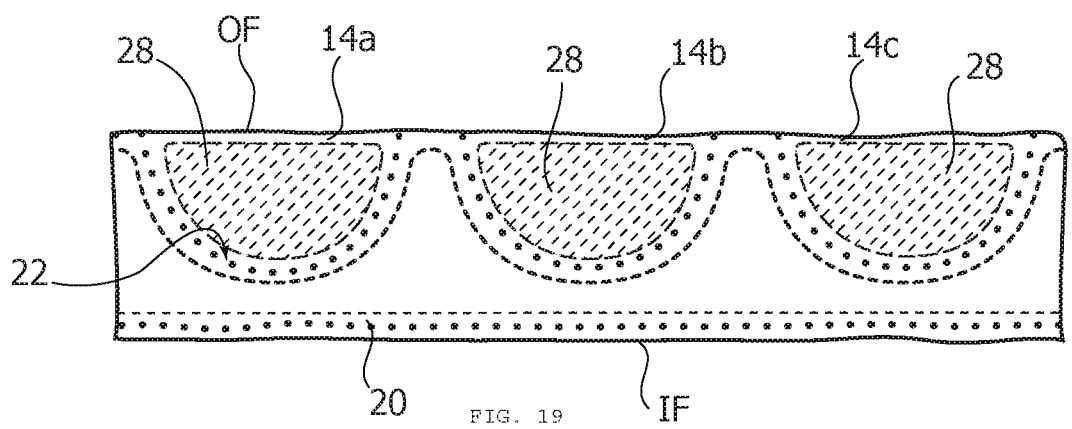
FIGS. 19 and 20a to 20d are exemplary of the possible use of pad members in the leaflets of a valvular sleeve of one or more embodiments.
Figure 20A:
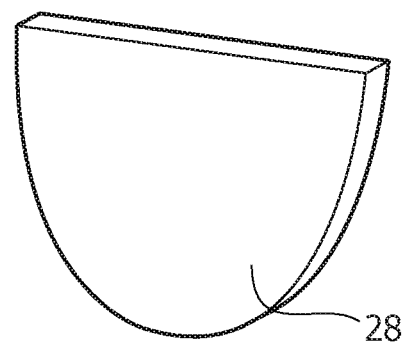
Figure 20B:
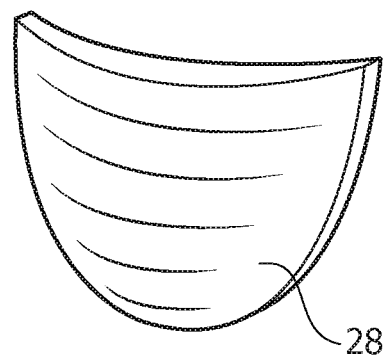
Figure 20C:
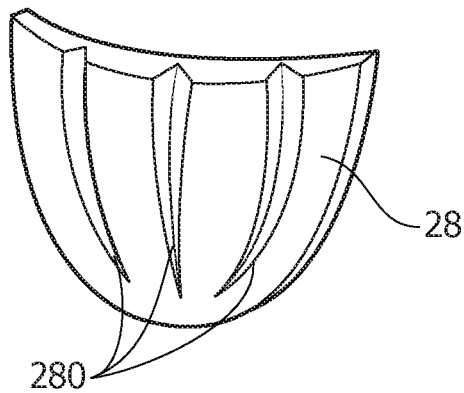
Figure 20D:
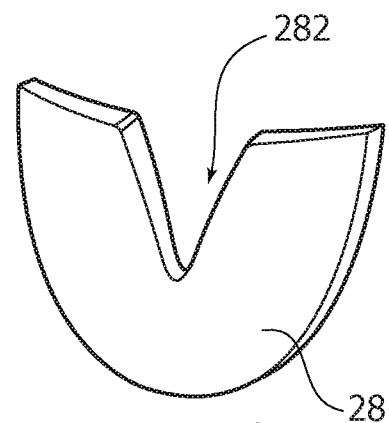

FIG. 19 is exemplary of the possibility of including pad members 28 in the space between the inner wall portion 141 and the outer wall portion 142 at the leaflet portions 14a, 14b, 14c.

In one or more embodiments, such pad members 28 may be generally crescent—shaped, semi-circular, semi-elliptical or eyelid-shaped (e.g. in the form of a shield), and may be scored or have notches cut in portions thereof, as schematically represented in parts a), b), c) and d) of FIG. 20. The pad members 28 may be planar or nearly planar, or may comprise a curved surface comprising a portion of a three-dimensional spherical body or a shape derived therefrom, as illustrated in parts b), c) and d) of FIG. 20. In one or more embodiments, the pad members 28 may include a flexible material.

In one or more embodiments, the pad members 28 may include a spongy material.

In one or more embodiments, the pad members 28 may have a surface sculpturing as exemplified at 280 in part c) of FIG. 20. This may facilitate following the rhythmic deformation that the leaflets 14a, 14b, 14c undergo (e.g. under pulsating blood pressure) in operation.

In one or more embodiments, the pad members 28 may include e.g. at their distal rim, at least one notch 282 which may bestow on the pad member an overall V or U shape. The notch or notches 282 may facilitate the closing and opening movement of the corresponding leaflet, that is the movement of the leaflet portions under fluid pressure between an inward condition to impede fluid flow from the outflow end OF to the inflow end IF and an outward condition to permit fluid flow from the inflow end IF to the outflow end OF.

In one or more embodiments, the pad members 28 may be retained at their location and prevented from being dislodged distally of the valvular sleeve 14 by the loop or fold between the inner portion 141 and the outer portion 142 at the outflow end OF of the valvular sleeve 14.

In one or more embodiments, the joining lines 24, 26 and/or the pad members 28 (possibly provided with the sculpturing 280 and/or the notch(es) 282) may be functional in bestowing onto the leaflets 14a, 14b, 14c a "bi-stable" behaviour thus making the leaflets 14a, 14b, 14c capable of alternatively "snapping open" under inflow-to-outflow fluid (e.g. blood) pressure and "snapping closed" under reversed outflow-to-inflow fluid pressure.

The valvular sleeve 14 as exemplified herein may include a plurality of (e.g., three) double-walled valve leaflets 14a, 14b, 14c (with the stent 16, if present, including a matching plurality (e.g., three) prongs 162) equally extending angularly 120° around the main axis $X_{160}$.

One or more embodiments may include a different number of leaflets and/or leaflets of different sizes. For instance, embodiments for use e.g. in venous valves may include two leaflets or even just one leaflet. Valvular sleeves for implantation at, e.g., a mitral site may include a higher number of leaflets e.g. four leaflets, possibly of different sizes.

One or more embodiments are largely independent of the number and sizes of the leaflets in the valvular sleeve 14.

FIGS. 21 to 28 are exemplary of possible embodiments wherein a valvular sleeve 14 may have a tapered shape from a (larger) inflow end IF towards a (narrower) outflow end OF. Such a tapered configuration may be regarded as more closely reproducing the anatomy of certain natural valves intended to be replaced with a valve prosthesis.

Figure 21:
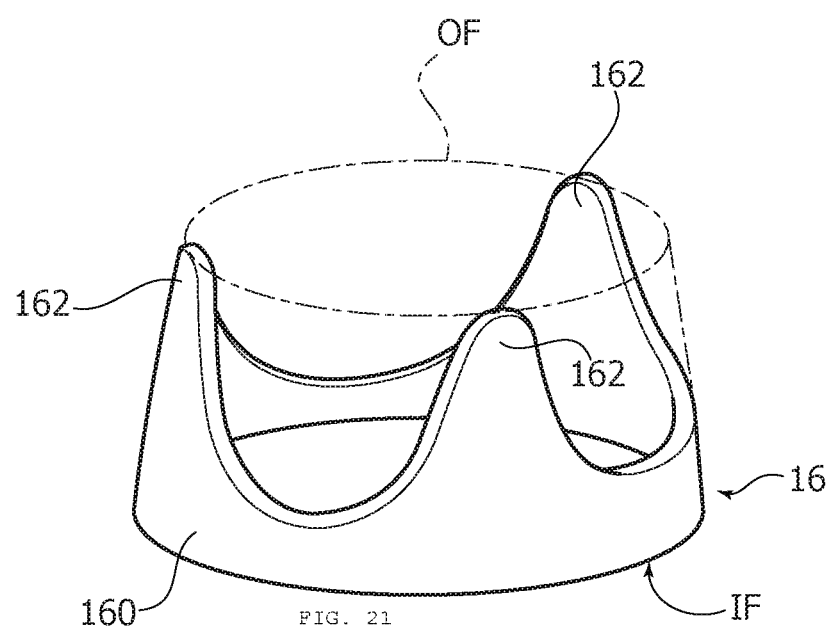
FIGS. 21 to 24 are exemplary of the production of tapered valvular sleeves.

As shown in FIG. 21, a stent (if contemplated) for such a valvular prosthesis may include prongs (posts) 162 which extend from a base body 160 in a distal direction from the inflow end IF to the outflow end OF with a general taper causing the distal ends of the prongs 162 to lie on an outflow circumference (as schematically indicated in chain line OF of FIG. 21) which has a smaller radius than the inflow end IF.

Figure 22:
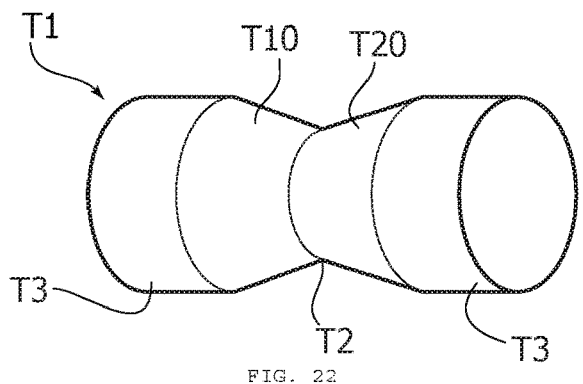
Figure 23:
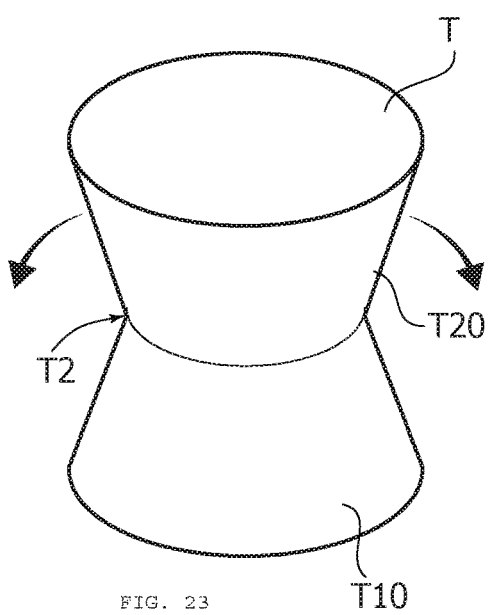
Figure 24:
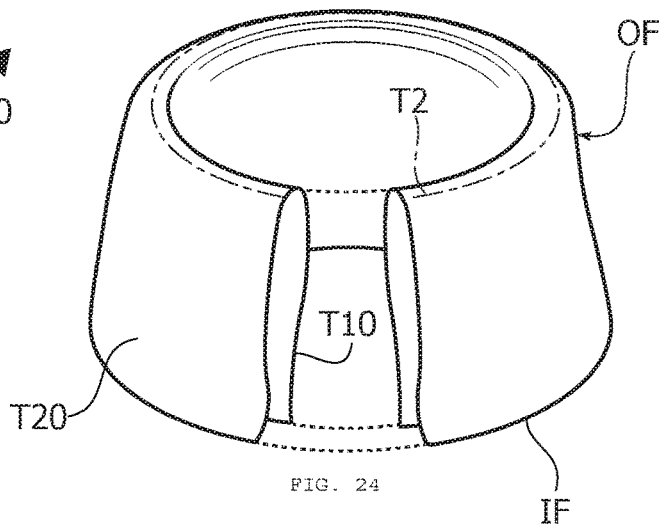
Figure 25:
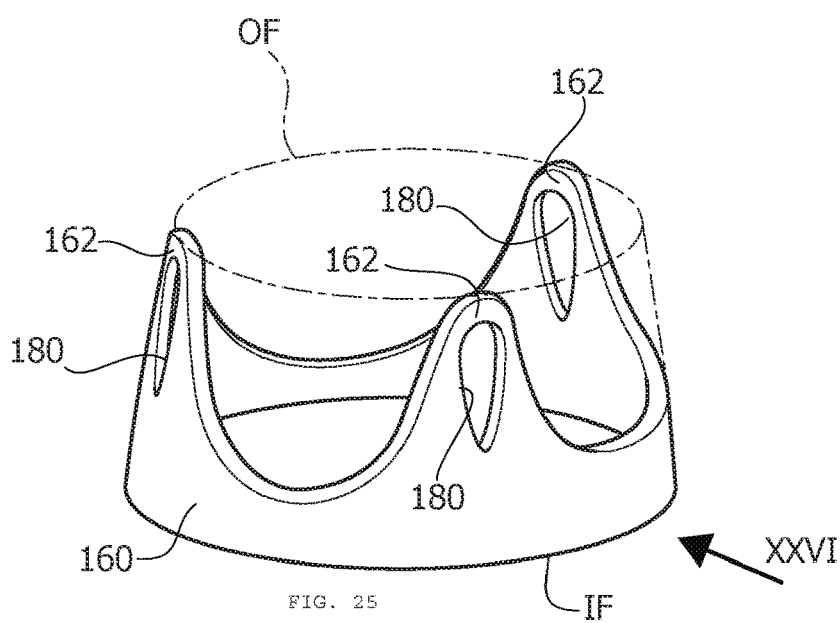
FIGS. 25 to 28 are exemplary of ways of mounting a valvular sleeve on a stent, with FIG. 26 an enlarged view of the portion of FIG. 25 indicated by the arrow XXVI and FIG. 28 a cross-sectional view along line XXVIII-XXVIII of FIG. 26.

FIGS. 22 to 24 are exemplary of one or more embodiments which may permit to produce a double-walled tubular body essentially similar to the tubular body as shown in FIG. 7. While still including sections T10, T20 adapted to form the inner portion 141 and the outer portion 142 (or vice versa) of the valvular sleeve 14 as discussed in the foregoing, the tubular body of FIG. 24 will exhibit an overall tapered (e.g. frusto-conical) shape.

The embodiment of FIGS. 22 to 24 is essentially similar (also as regards the possibility for the sections T10, T20 to exchange their roles in forming the inner and the outer portions 141, 142) to the embodiment of FIGS. 5A, 5B, 6 and 7. The related detailed description will not be repeated here for the sake of brevity, while noting that, in the case of FIGS. 22 to 24, the tubular sheet member T may be an hourglass-shaped tube with an overturning (folding) line T2 arranged at the waist line of the hourglass shape.

Such an hourglass-shaped tubular member T as shown in FIG. 23 may be produced e.g. by means of fabric knitting techniques adapted for use also for medical devices (e.g. vascular grafts). FIGS. 22 and 23 refer to a (non-mandatory) embodiment where the hourglass-shaped tubular sheet member T is produced starting from a longer tubular sheet member T1 (produced e.g. by a knitting process of a known type) including an intermediate hourglass-shaped portion which is isolated by cutting opposed cylindrical ends T3.

The tapered tubular body of FIG. 24 may then be used either in a tapered valvular prosthesis of the stentless type or in a tapered valvular prosthetic device 10 for a stented valvular prosthesis by being coupled with a stent 16 as exemplified in FIG. 21.

The related disclosure provided in connection with FIGS. 12 to 20 will thus apply (also) to such a tapered valvular sleeve 14/valvular prosthetic device 10.

FIGS. 25 to 28 exemplify one embodiment of a way of coupling a valvular sleeve 14 with a stent 16 by arranging the stent 16 surrounding the valvular sleeve 14 as schematically represented in FIG. 1.

FIGS. 25 to 28 exemplify such embodiments in connection with a tapered valvular sleeve 14/stent 16. The same concepts may apply also to a non-tapered valvular sleeve 14/stent 16 as discussed previously in this description.

Figure 26:
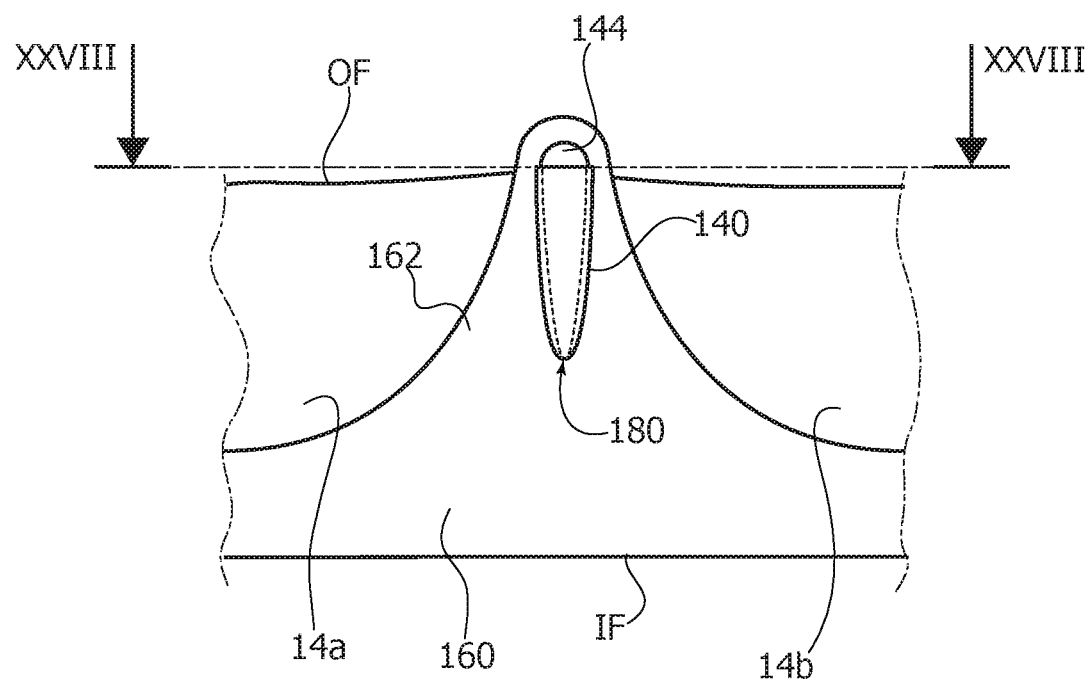
Figure 27:
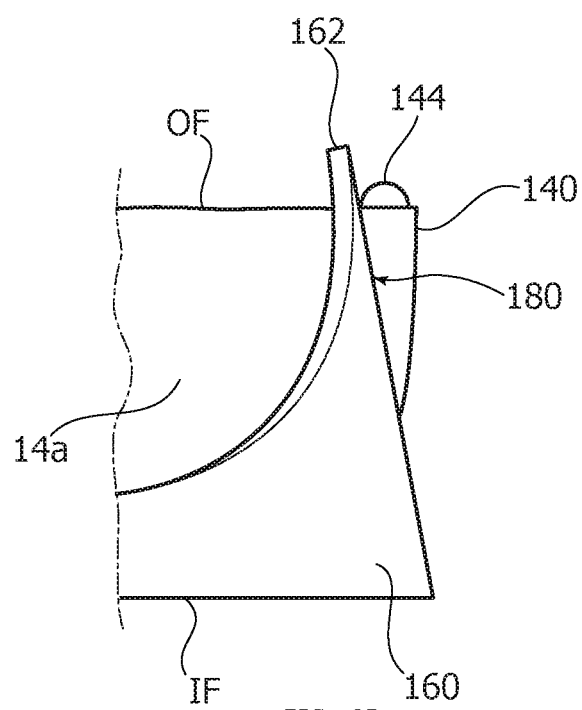
Figure 28:
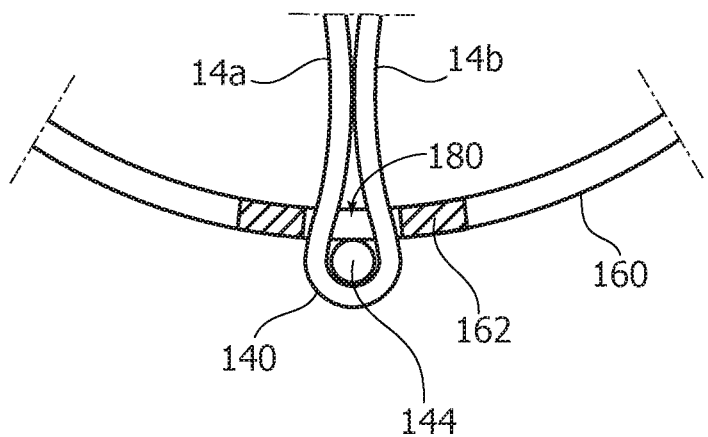

In one or more embodiments as exemplified in FIGS. 25 to 28 the prongs 162 extending distally of the main body 162 from the inflow end IF to the outflow end OF may include a longitudinal slit or aperture 180 into which a folded portion 140, formed e.g. at one of the commissures of the valvular sleeve 14, may be inserted as shown e.g. in FIGS. 26 to 28.

In that way, the valvular sleeve 14 will essentially extend within a portion of the stent 16, that is with the stent 16 largely surrounding the valvular sleeve 14. However, the folded portions 140, will at least marginally extend at the outer surface of the stent 16 so that a peg member 144 may be inserted into each folded portion 140 to provide anchoring of the commissures of valvular sleeve 14 to the prongs 162.

That mounting arrangement may be applied also in the case on non-tapered (e.g. cylindrical) valvular sleeves 14/stents 16.

In one or more embodiments (related to a tapered valvular prosthesis 10 as exemplified in FIGS. 25 to 28) the slits or apertures 180 may be provided with an increasing width (e.g. with a sort of "raindrop" shape) in the distal direction of the stent 16, namely with a width increasing away from the body portion 160.

The peg members 144 may be inserted wedge-like into the folded portions 140 in such a way that the folded portions 140 will be widening towards the outflow end OF of the valvular sleeve. The circumferential extension, and thus the radial size of the valvular sleeve 14 within the stent 16 will thus be smaller at the outflow end OF in comparison with the inflow end IF: this is because the folded portions 140 will "draw" more material of the valvular sleeve 14 out of the stent 16 at the outflow end OF than at the inflow end IF. The "effective" valvular sleeve 14 surrounded by the stent 16 will then have a tapered shape as in the case of the tapered tubular body of FIG. 24.

Figure 29:
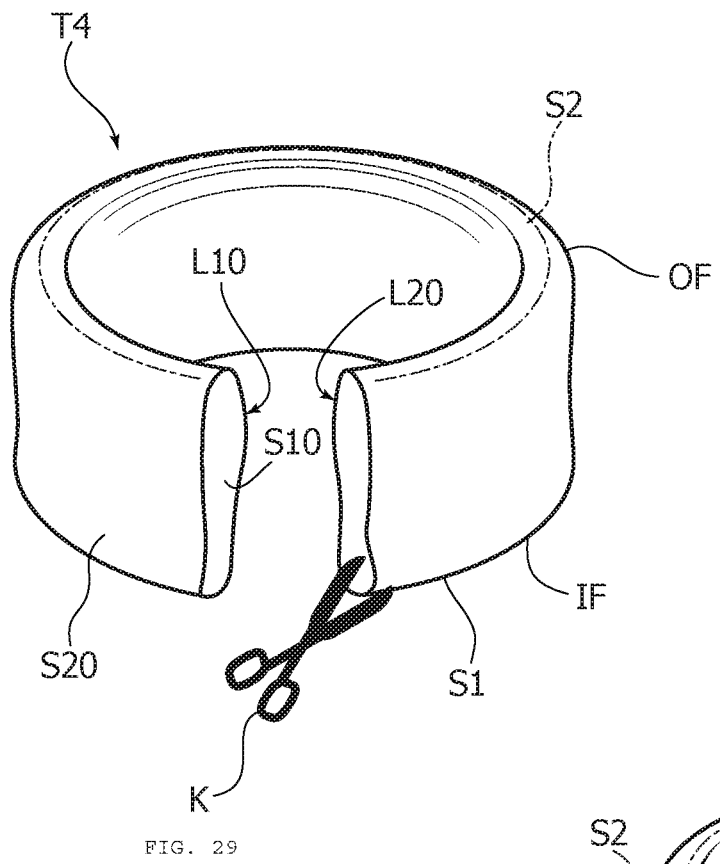
FIGS. 29 and 30 are exemplary of the production of valvular sleeves for valvular prostheses according to one or more embodiments.
Figure 30:
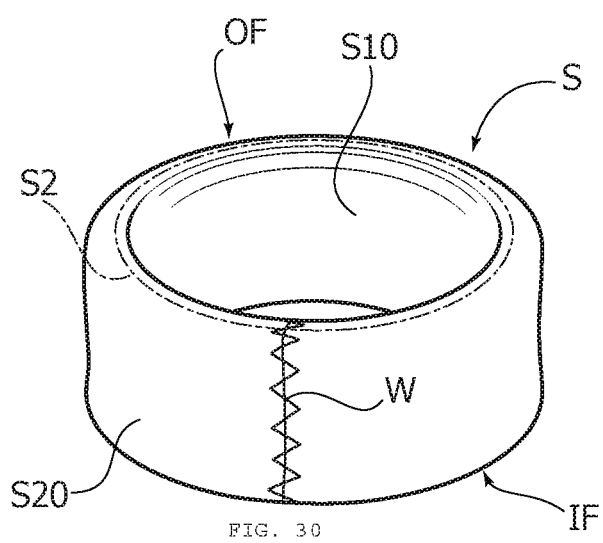

FIGS. 29 and 30 are exemplary of still another way of producing a tubular body as exemplified e.g. in FIG. 11 for use in any of the embodiments exemplified herein.

In FIGS. 29 and 30 a tubular sheet member T4 may again be used. Instead of being overturned at an overturn line T2 as exemplified in FIG. 6, the tubular member T4, possibly flattened to a general ribbon-like shape, may be formed into a ring or collar as schematically shown in FIG. 29, thus undergoing the same type of shaping as discussed in connection with FIG. 10. Once formed into a ring or collar, the tubular member T4 will have opposed ends, again designated L10, L20, which may be joined to each other at a joining line W to form a tubular body adapted for use as a valvular sleeve 14 as disclosed in the foregoing.

Once formed into a ring or collar, the tubular member T4 will in fact have two opposed loop portions designated S2 and S1 in FIG. 29. One of these loop portions at the sides of the flattened tubular member T4 shaped into a ring or collar may in fact correspond to a folding line S2 forming a loop between the two wall portions of the ribbon-like tubular member. Such a folding line S2 may again be located at the outflow end OF of the tubular sleeve 14 as exemplified previously in connection with FIGS. 10 to 13.

As exemplified by a scissor K in FIG. 29, the loop portion S1 may be cut in order to open the tubular body at the end opposed the folding line S2 as in the case of the tubular body of FIG. 11. This will permit insertion of a stent 16 into the valvular sleeve as schematically shown in FIGS. 12 and 14.

In one or more embodiments, the opposed walls S10 and S20 of the tubular member T4 may be left connected at both lines S2 and S1. This may apply e.g. to "stentless" valvular prostheses for which coupling to a support stent 16 may not be envisaged or to those embodiments were coupling with a stent 16 may occur either by causing the stent 16 to surround the valvular sleeve 14 (see e.g. FIG. 1) or by causing the valvular sleeve 14 to surround the stent 16, so that the space between the inner portion 141 and the outer portion 142 may not need to be made open for permitting insertion of a stent 16 therein.

For instance, an arrangement wherein the inner and outer portions 141, 142 of the valvular sleeve 14 have a loop or fold therebetween at both the inflow end IF and the outflow end OF (that is at the distal margins of the leaflets 14a, 14b, 14c) may be adapted for coupling to a stent using the slit/aperture and peg arrangement as exemplified in FIGS. 25 to 28.

In one or more embodiments a double-walled tubular body as exemplified in FIG. 30 may be produced by knitting methods (e.g. by means of circular knitting machines) as a single body, thus dispensing with the need of providing a joining line W.

One or more embodiments may thus include a plurality of (e.g. three) valve leaflet portions extending distally of said inflow end towards distal margins at said outflow end.

In one or more embodiments, the valve leaflets may be displaceable under fluid pressure to an inward, "closed" condition wherein the distal margins of the leaflets coapt to impede fluid flow from said outflow end to said inflow end.

In one or more embodiments, the inner and outer portions 141, 142 of the (double-walled) leaflets 14a, 14b, 14c may be formed of a single piece of sheet material with a fold or loop (e.g. the folding line S2) therebetween at the outflow end OF (that is, at the distal margins of the leaflets 14a, 14b, 14c).

In the following, examples are described to facilitate the understanding of embodiments.

In some embodiments: A valvular sleeve for valvular prostheses including a tubular body extending between an inflow end and an outflow end, the tubular body including a sheet member folded at said outflow end, whereby the tubular body includes an inner tubular portion and an outer tubular portion surrounding the inner tubular portion.

In some embodiments: The valvular sleeve of Embodiment 1, wherein said inner and outer portions comprise either of:
 respective subsequent sections of a tubular member overturned at an overturn line at said outflow end;
 respective portions of a sheet member U-folded at a folding line at said outflow end, said U-folded sheet member having opposed end edges joined to each other to form said tubular body.

In some embodiments: The valvular sleeve of Embodiment 1 or Embodiment 2, wherein said inner and outer portions are joined to each other, optionally by suture, at said inflow end.

In some embodiments: The valvular sleeve of Embodiment 1, wherein said inner and outer portions comprise respective wall portions of a tubular ribbon-like member, optionally having opposed ends joined to each other to form said tubular body.

In some embodiments: The valvular sleeve of any of the previous Embodiments, wherein said inner and outer portions include valve leaflet portions extending distally of said inflow end towards said outflow end, said valve leaflet portions displaceable under fluid pressure to an inward condition to impede fluid flow from said outflow end to said inflow end and an outward condition to permit fluid flow from said inflow end to said outflow end.

In some embodiments: The valvular sleeve of Embodiment 5, wherein said inner and outer portions are joined to each other, preferably by suture, at said valve leaflet portions.

In some embodiments: The valvular sleeve of Embodiment 6, wherein said inner and outer portions are joined to each other at said valve leaflet portions by at least one of:
- a scalloped joining line extending at a proximal edge of said leaflet portions,
- a pattern of joining lines extending distally of a proximal edge of said leaflet portions.

In some embodiments: The valvular sleeve of any of Embodiments 5 to 7, including a pad member set between said inner and outer sheets at said valve leaflet portions.

In some embodiments: The valvular sleeve of any of the previous Embodiments, wherein said inner and outer portions comprise respective subsequent sections of an hourglass-shaped tubular sheet member overturned at an overturn line at the waistline of the hourglass shape, said overturn line being at said outflow end of the valvular sleeve, whereby said valvular sleeve has a tapered shape from said inflow end towards said outflow end.

In some embodiments: A prosthetic valvular device including:
- a valvular sleeve according to any of Embodiments 1 to 9,
- a stent supporting said valvular sleeve.

In some embodiments: The prosthetic valvular device of Embodiment 10, including anchoring formations, optionally suture formations, anchoring said valvular sleeve to said stent.

In some embodiments: The prosthetic valvular device of Embodiment 10 or Embodiment 11, wherein said stent extends between said inner and outer portions of the valvular sleeve.

In some embodiments: The prosthetic valvular device of Embodiment 10 or Embodiment 11, wherein:
- said stent is arranged surrounding said valvular sleeve and includes a ring-like body at said inflow end of the valvular sleeve with a plurality of prongs extending from said ring-like body in a distal direction from said inflow end towards said outflow end of the valvular sleeve,
- said prongs have a longitudinal slit,
- said valvular sleeve includes folded portions which extend through the longitudinal slits of said prongs externally of said stent, and
- peg members are inserted into said folded portions of the valvular sleeve externally of said stent to provide anchoring of said valvular sleeve to the stent.

In some embodiments: The prosthetic valvular device of Embodiment 13, wherein:
- said prongs extend distally of said ring-like body from said inflow end towards said outflow end of the valvular sleeve with a tapered shape of said stent,
- said prongs have a longitudinal slit having an increasing width in said distal direction, and
- said peg members are inserted wedge-like into said folded portions of the valvular sleeve to provide anchoring of said valvular sleeve to the stent, wherein the valvular sleeve is radially larger at said inflow end than at said outflow end.

In some embodiments: The prosthetic valvular device of any of embodiments 10 to 14, wherein said stent is collapsible.

Without prejudice to the underlying principles, the details and embodiments may vary, even significantly, with respect to what has been described by way of the example only, without departing from the extent of protection.

The extent of protection is defined by the annexed claims.

The invention claimed is:

1. A valvular heart prosthesis, comprising:
   a valvular sleeve including a tubular body extending between an inflow end and an outflow end, the tubular body including a sheet member folded at said outflow end, whereby the tubular body includes an inner tubular portion and an outer tubular portion surrounding the inner tubular portion;
   wherein each of the inner tubular portion and the outer tubular portion includes valve leaflet portions that cooperate to form double-walled valve leaflets that extend distally of the inflow end and towards the outflow end, the double-walled valve leaflets displaceable under fluid pressure to an inward condition to impede fluid flow from the outflow end to the inflow end and an outward condition to permit fluid flow from the inflow end to the outflow end; and
   a stent supporting the valvular sleeve and positioned between the inner tubular portion and the outer tubular portion directly adjacent the valve leaflet portions, the stent positioned at the fold of the sheet member at the outflow end and positioned slightly spaced from an inflow edge of the inflow end to accommodate a joining line for joining together the inner tubular portion and the outer tubular portion,
   wherein the inner tubular portion and the outer tubular portion of the valvular sleeve are joined together at the inflow end to couple the valvular sleeve to the stent.

2. The valvular heart prosthesis of claim 1, wherein said inner and outer tubular portions comprise at least one of:
   respective subsequent sections of a tubular member overturned at an overturn line at said outflow end; and
   respective portions of a sheet member U-folded at a folding line at said outflow end, said
   U-folded sheet member having opposed end edges joined to each other to form said tubular body.

3. The valvular heart prosthesis of claim 1, wherein said inner and outer tubular portions comprise respective wall portions of a tubular ribbon-like member.

4. The valvular heart prosthesis of claim 1, wherein said inner and outer tubular portions are joined to each other at said valve leaflet portions.

5. The valvular heart prosthesis of claim 4, wherein said inner and outer tubular portions are joined to each other at said valve leaflet portions by at least one of:
   a scalloped joining line extending at a proximal edge of said valve leaflet portions, and
   a pattern of joining lines extending distally of a proximal edge of said valve leaflet portions.

6. The valvular heart prosthesis of claim 1, including a pad member set between said inner and outer tubular portions at said valve leaflet portions.

7. The valvular heart prosthesis of claim 1, wherein said inner and outer tubular portions comprise respective subsequent sections of an hourglass-shaped tubular sheet member overturned at an overturn line at a waistline of the hourglass shape, said overturn line being at said outflow end of the valvular sleeve, whereby said valvular sleeve has a tapered shape from said inflow end towards said outflow end.

8. The valvular heart prosthesis of claim 1, wherein said stent extends between said inner and outer tubular portions of the valvular sleeve.

9. The valvular heart prosthesis of claim 1, wherein said stent is collapsible.

10. A prosthetic valvular device, comprising:
a valvular sleeve for valvular prostheses including a tubular body extending between an inflow end and an outflow end, the tubular body including a sheet member folded at said outflow end, whereby the tubular body includes an inner tubular portion and an outer tubular portion surrounding the inner tubular portion, the inner tubular portion and the outer tubular portion having a same length from the inflow end to a fold line at the outflow end;
wherein each of the inner tubular portion and the outer tubular portion includes valve leaflet portions that cooperate to form double-walled valve leaflets that extend distally of the inflow end and towards the outflow end, the double-walled valve leaflets displaceable under fluid pressure to an inward condition to impede fluid flow from the outflow end to the inflow end and an outward condition to permit fluid flow from the inflow end to the outflow end; and
a stent including prongs that support the valvular sleeve, such that each of the double-walled valve leaflets is situated between two of the prongs, wherein the valvular sleeve includes anchoring formations that anchor the valvular sleeve to the stent at the inflow end and that join together only the inner tubular portion and the outer tubular portion of the valvular sleeve at the inflow end.

11. The prosthetic valvular device of claim 10, wherein said inner and outer tubular portions comprise at least one of:
respective subsequent sections of a tubular member overturned at the fold line at said outflow end; and
respective portions of a sheet member U-folded at the fold line at said outflow end, said U-folded sheet member having opposed end edges joined to each other to form said tubular body.

12. The prosthetic valvular device of claim 10, wherein said inner and outer tubular portions comprise respective wall portions of a tubular ribbon-like member.

13. The prosthetic valvular device of claim 10, wherein said inner and outer tubular portions are joined to each other at said valve leaflet portions.

14. The prosthetic valvular device of claim 13, wherein said inner and outer tubular portions are joined to each other at said valve leaflet portions by at least one of:
a scalloped joining line extending at a proximal edge of said valve leaflet portions, and
a pattern of joining lines extending distally of a proximal edge of said valve leaflet portions.

15. The prosthetic valvular device of claim 10, including a pad member set between said inner and outer tubular portions at said valve leaflet portions.

16. The prosthetic valvular device of claim 10, wherein said inner and outer tubular portions comprise respective subsequent sections of an hourglass-shaped tubular sheet member overturned at the fold line at a waistline of the hourglass shape, said fold line being at said outflow end of the valvular sleeve, whereby said valvular sleeve has a tapered shape from said inflow end towards said outflow end.

17. The prosthetic valvular device of claim 10, wherein said stent extends between said inner and outer tubular portions of the valvular sleeve.

18. The prosthetic valvular device of claim 10, wherein said stent is collapsible.

19. A prosthetic valvular device, comprising:
a valvular sleeve for valvular prostheses including a tubular body extending between an inflow end and an outflow end, the tubular body including a sheet member folded at said outflow end, whereby the tubular body includes an inner tubular portion and an outer tubular portion surrounding the inner tubular portion;
wherein each of the inner tubular portion and the outer tubular portion includes valve leaflet portions that cooperate to form double-walled valve leaflets that extend in a distal direction of the inflow end and towards the outflow end, the double-walled valve leaflets displaceable under fluid pressure to an inward condition to impede fluid flow from the outflow end to the inflow end and an outward condition to permit fluid flow from the inflow end to the outflow end; and
a stent including prongs that support the valvular sleeve, said stent positioned to surround the valvular sleeve, wherein:
said stent includes a ring-like body at said inflow end of the valvular sleeve with a plurality of prongs extending from said ring-like body in a distal direction from said inflow end towards said outflow end of the valvular sleeve,
said prongs have a longitudinal slit,
said valvular sleeve includes folded portions which extend through the longitudinal slits of said prongs externally of said stent, and
peg members are inserted into said folded portions of the valvular sleeve externally to said stent to provide anchoring of said valvular sleeve to the stent.

20. A prosthetic valve of claim 19, wherein a distal end of the prongs lies on an outflow circumference that has a lesser radius than a radius of an inflow end circumference from which the prongs extend.

* * * * *